United States Patent
Pang et al.

(10) Patent No.: US 10,092,266 B2
(45) Date of Patent: Oct. 9, 2018

(54) METAL ARTIFACT CORRECTION AND NOISE-ADJUSTMENT OF CT SCAN IMAGE

(71) Applicant: Shenyang Neusoft Medical Systems Co., Ltd., Shenyang (CN)

(72) Inventors: Ling Pang, Shenyang (CN); Junlong Han, Shenyang (CN); Shanshan Lou, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 244 days.

(21) Appl. No.: 14/918,596

(22) Filed: Oct. 21, 2015

(65) Prior Publication Data
US 2016/0110893 A1   Apr. 21, 2016

(30) Foreign Application Priority Data
Oct. 21, 2014   (CN) .......................... 2014 1 0562585

(51) Int. Cl.
*G06K 9/00*   (2006.01)
*A61B 6/00*   (2006.01)
*G06T 11/00*   (2006.01)

(52) U.S. Cl.
CPC .......... *A61B 6/5258* (2013.01); *A61B 6/5205* (2013.01); *G06T 11/005* (2013.01)

(58) Field of Classification Search
None
See application file for complete search history.

(56) References Cited

U.S. PATENT DOCUMENTS

| 5,909,476 A * | 6/1999 | Cheng ................... G06T 11/006 378/4 |
| 8,233,586 B1 * | 7/2012 | Boas ..................... G06T 11/005 378/207 |
| 2008/0095462 A1 | 4/2008 | Hsieh et al. |

(Continued)

FOREIGN PATENT DOCUMENTS

| CN | 102567958 A | 7/2012 |
| CN | 103218777 A | 7/2013 |

(Continued)

OTHER PUBLICATIONS

Watzke, O., & Kalender, W. A. (2004). A pragmatic approach to metal artifact reduction in CT: merging of metal artifact reduced images. European radiology, 14(5), 849-856.*

(Continued)

*Primary Examiner* — Vu Le
*Assistant Examiner* — Samah Beg
(74) *Attorney, Agent, or Firm* — Kilpatrick Townsend & Stockton, LLP

(57) ABSTRACT

A method for correcting a CT scan image is provided. A target image including a target region to be corrected is extracted from an original CT scan image. A target projection range corresponding to the target region is obtained by orthographically projecting the target image, and target projection data within the target projection range is corrected. Noise of the corrected target projection data is adjusted to generate noise-adjusted target projection data to improve noise consistency between target region and the rest of the CT scan image. A corrected CT scan image is reconstructed based on the noise-adjusted target projection data.

10 Claims, 4 Drawing Sheets

(Abstract companying figure)

(56) References Cited

U.S. PATENT DOCUMENTS

| | | | | |
|---|---|---|---|---|
| 2008/0273651 | A1* | 11/2008 | Boas | G06T 11/005 378/4 |
| 2010/0073522 | A1* | 3/2010 | Siddiqui | G06T 5/002 348/241 |
| 2010/0183214 | A1* | 7/2010 | McCollough | A61B 6/032 382/131 |
| 2010/0215230 | A1* | 8/2010 | Bornefalk | G06T 11/005 382/128 |
| 2011/0075905 | A1 | 3/2011 | Noshi et al. | |
| 2012/0019512 | A1* | 1/2012 | Yang | G06T 11/005 345/419 |
| 2012/0177274 | A1 | 7/2012 | Koehler et al. | |
| 2013/0004042 | A1* | 1/2013 | Yang | G06T 11/005 382/131 |
| 2013/0051674 | A1* | 2/2013 | Goossens | G06T 5/002 382/173 |
| 2013/0089252 | A1* | 4/2013 | Shechter | G06T 5/002 382/131 |
| 2013/0112874 | A1* | 5/2013 | Osvath | A61B 6/486 250/311 |
| 2015/0069257 | A1* | 3/2015 | Besson | G01T 1/1647 250/394 |
| 2015/0146955 | A1* | 5/2015 | Dong | G06T 11/008 382/131 |
| 2015/0187052 | A1* | 7/2015 | Amroabadi | A61B 6/5205 382/131 |
| 2015/0355114 | A1* | 12/2015 | Taguchi | A61B 6/4241 378/62 |
| 2016/0125625 | A1* | 5/2016 | Kim | G06T 11/003 382/131 |
| 2016/0143604 | A1* | 5/2016 | Lou | A61B 6/032 378/20 |
| 2017/0213365 | A1* | 7/2017 | Koehler | G06T 11/003 |

FOREIGN PATENT DOCUMENTS

| | | |
|---|---|---|
| CN | 103310432 A | 9/2013 |
| CN | 103501702 A | 1/2014 |
| CN | 103679642 A | 3/2014 |
| CN | 103732147 A | 4/2014 |
| EP | 2149284 B1 | 8/2014 |

OTHER PUBLICATIONS

Wang G, Snyder DL, O'Sullivan JA, et al. Iterative deblurring for CT metal artifact reduction. IEEE Transactions on Medical Imaging, vol. 15, No. 5, Oct. 1996.

Sun Shuwen, Luo Shouhua; An Approach to Metal Artifact Reduction in CT Images; Sciencepaper Online Jun. 1, 2009 1-5 pages.

* cited by examiner

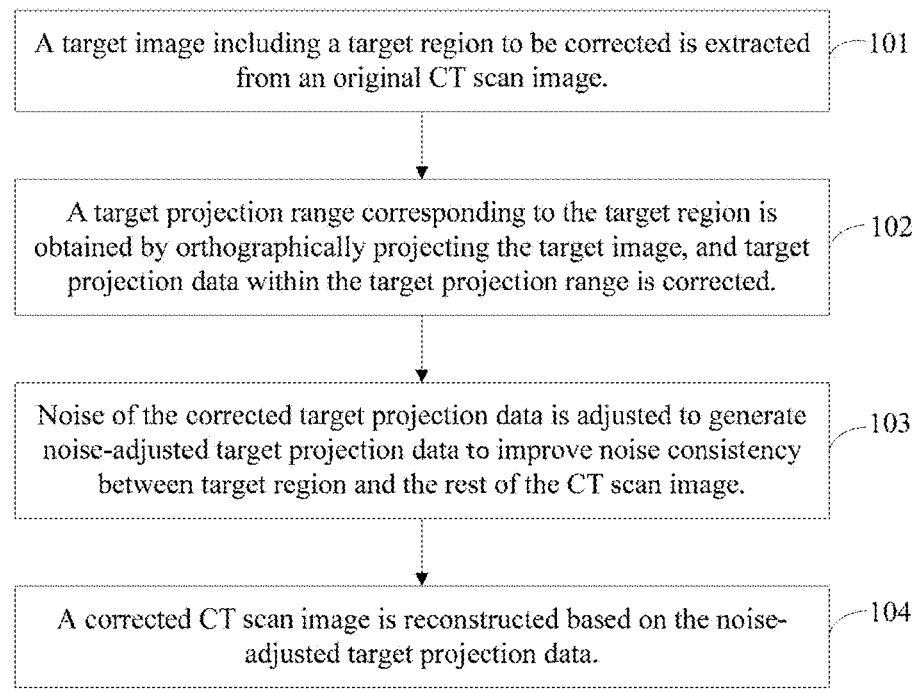
FIG. 1 (Abstract companying figure)
FIG. 2

METAL ARTIFACT CORRECTION AND NOISE-ADJUSTMENT OF CT SCAN IMAGE

The present application claims the priority to Chinese Patent Applications No. 201410562585.6, titled "CORRECTING A CT SCAN IMAGE", filed with the Chinese State Intellectual Property Office on Oct. 21, 2014, which is incorporated herein by reference in its entirety.

BACKGROUND

The present disclosure is directed to computed tomography (CT).

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

As described below, inconsistencies of the whole noise may exist in CT scan image due to correction. This may result in poor reconstruction image quality. Hence, it is desirable to have improved methods and devices for correcting a CT scan image.

BRIEF DESCRIPTION OF DRAWINGS

Features of the present disclosure are illustrated by way of example and not limited in the following figure(s), in which like numerals indicate like elements, in which:

FIG. 1 is a schematic flowchart illustrating the procedures of a method for correcting a CT scan image according to an example of the present disclosure;

FIG. 2 is an original CT scan image of the example shown in FIG. 1;

DETAILED DESCRIPTION

Figure 3:
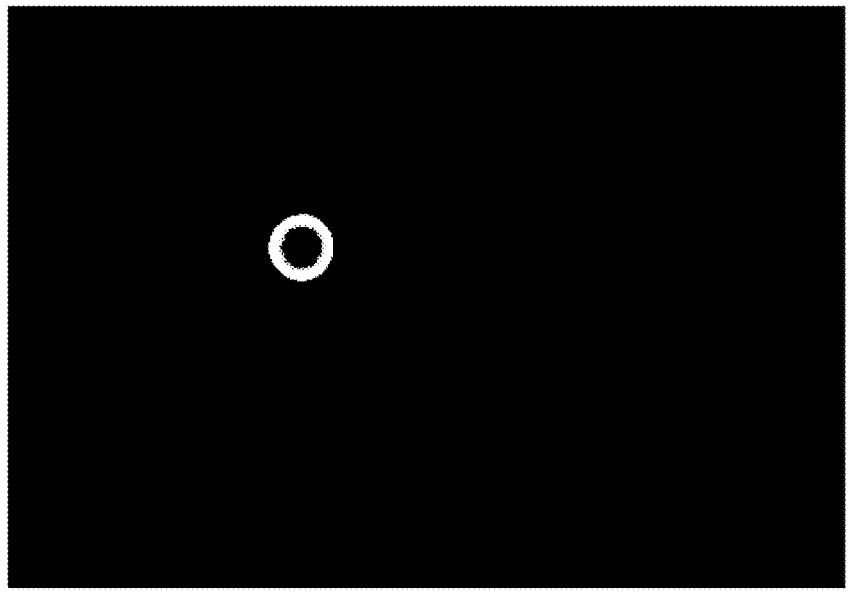
FIG. 3 is a metal region image obtained by dividing thresholds of the original CT scan image shown in FIG. 2.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

A CT (computed tomography) device uses X-ray beams and detectors to revolve a certain region of a subject for performing a continuous cross-section scanning, and it has characteristics such as fast scanning time and image clarity and can be used for examining a variety of diseases. When the CT device uses CT scanning data for reconstructing CT scan image of the scanned subject, a noise inconsistency may exist in the reconstructed image if the attenuation difference of the scanning subject within the scanning range is too large. For example, if a metal is included in the subject, due to serious X-ray beam hardening, increasing noise, scattering effect, and partial volume effect, serious metal artefacts may occur.

During the process of correcting CT scan image, the data containing metal artefacts is corrected in order to prevent metal artefacts from affecting reconstruction of CT scan image. However, inventors of present disclosure through study found that, the image noise of the region having metal artefacts corrected is not consistent with the image noises of other uncorrected adjacent image regions. This noise inconsistency in the CT scan image makes the image quality of the reconstructed CT scan image poor.

The present disclosure is directed to correcting the above-mentioned noise inconsistency in a CT scan image. Embodiments are provided to correct noise of data within a CT scan image region having metal artefacts corrected such that noise or noise level in this region is consistent with that of the rest of the CT image.

FIG. 1 is a flowchart illustrating the procedures of a method for correcting a CT scan image according to an example of the present disclosure.

At block 101, a target image including a target region to be corrected is extracted from an original CT scan image.

In this example, correction for the target region with larger attenuation is required, such as the target region with serious metal artefacts. Therefore, the target image including the target region to be corrected can be first extracted from the original CT scan image. In the following description, the target image including a metal target region is taken as an example. However, it should be understood that, the method of the present disclosure is not limited to being applied to a subject containing metal.

FIG. 2 is a screenshot of an original CT scan image containing a metal artefact. The metal artefact of the original CT scan image is very serious, and usually cannot be directly used in actual clinical diagnosis. Hence, a predetermined method is used for extracting the target image including the metal target region in the present disclosure. There are many predetermined extracting methods. For example, a threshold segmentation method can be adopted. Since pixel values of the metal target region are usually much higher than pixel values in other regions, an appropriate threshold (for example, the pixel value is 2000) can be selected for extracting the target image including the metal target region.

FIG. 3 is a target image including a target region to be corrected.

Referring to FIG. 1, at block 102, a target projection range corresponding to the target region is obtained by orthographically projecting the target image, and target projection data within the target projection range is corrected.

Sinogram tracks of the metal can be obtained by orthographically projecting the target image including the metal target region at each projection angle, and then the orthographic projection data of the metal target region of the target image within the target projection range can be obtained. For the convenience of description, the orthographic projection data within the range is called as the target projection data in the present disclosure, and it usually is the cause of metal artefacts. Hence, at this block, the target projection data within the target projection range requires correction. The target projection range means positions corresponding to the projection data obtained by orthographically projecting the metal target region of the target image.

In an example, the step of correcting target projection data within the target projection range at the block 102 may further include the following steps.

At block A1, a linear interpolation value of two projection data points located at two adjacent sides of the target projection data is obtained.

During the process of correcting the target projection data within the target projection range, a linear interpolation sinogram correction method can be used for calculating the corrected image of the target projection data, and a linear interpolation value of two projection data points located at two adjacent sides of the target projection data can be calculated by using the two projection data points.

At block A2, the target projection data is replaced with the linear interpolation value so as to obtain corrected data of the target projection data.

At block A3, a corresponding corrected image is reconstructed according to the corrected data of the target projection data.

At block A4, a reference image of the corrected image is determined according to a default segmentation threshold.

In an example, a reference image of the corrected image can be obtained according to default segmentation thresholds. In a CT scan image, there are different data corresponding to soft tissue, bone, and air, respectively. In this example, two appropriate thresholds can be selected first, wherein a first threshold t1 is used for differentiating air and soft tissue, and a second threshold t2 is used for differentiating soft tissue and bone. These two thresholds can be a median value of the average CT values of the two substances. After separating air, soft tissue, and bone of the CT scan image, assuming that the data of air is set as −1000 HU, the data of soft tissue is set as 0 HU, the data of bone is set to maintain its original value, and the data of the metal is set as the CT value of the soft tissue (i.e., 0 HU), the reference image can be calculated and obtained by using the corrected image.

At block A5, the reference image is orthographically projected so as to obtain reference projection data of the reference image.

At block A6, the reference projection data is determined as the corrected target projection data.

The target projection data is replaced with the reference projection data of the reference image, and is used as the corrected target projection data. Therefore, through the blocks A1-A6, all data for generating metal artefacts can be eliminated, but corresponding data of the metal is eliminated at the same time.

At block 103, noise of the corrected target projection data is adjusted to generate noise-adjusted target projection data to improve noise consistency between target region and the rest of the CT scan image.

Usually, in the corrected target projection data, the noise of the data in the metal target region is inconsistent with the noise of the data in other non-metal regions. For example, at block A4, the reference image is obtained by using a threshold segmentation method, wherein there is no noise and the noise value is zero. The reference projection data of the reference image is used for correcting the target projection data, and thus the noise of the corrected target projection data is almost zero. Therefore, in order to make the data of the junction between the projection data of the metal target region and the projection data of the non-metal region smooth, the noise of the target projection data needs to be adjusted so as to make its noise value consistent with the noise value of the non-target projection data. This improves the whole noise consistency of the reconstructed CT scan image.

In an example, the step of adjusting noise of the corrected target projection data to generate noise-adjusted target projection data to improve noise consistency between target region and the rest of the CT scan image may include the following steps.

At block B1, the target projection data of an attenuation domain is converted into target projection data of an intensity domain.

Usually, the noise of the original raw data acquired by CT detector is mainly quantum noise, wherein the quantum noise is a noise with a Poisson distribution and uses the photon number received by the CT detector as its parameter. Therefore, the corrected target projection data can be extracted, and then the target projection data P of an attenuation domain can be converted into target projection data I of an intensity domain (i.e., the data collected by the CT detector). The conversion can be shown in the following formula (1).

$$I = I_0 \cdot e^{-P} \quad (1);$$

$I_0$ means the original scanning current of X-ray, and can be set as the intensity value that CT does not scan objects or the intensity value received while scanning air; e means a natural base; and p means the target projection data of the attenuation domain.

At block B2, the target projection data of the intensity domain is multiplied by a default transform coefficient so as to obtain a transformed target projection data.

Usually, a fixed constant ratio exists between the photon number received by the CT detector and the target projection data of the intensity domain, which is called a transform coefficient W. In this example, a predetermined conversion method can be used for converting the target projection data I of the intensity domain into the target projection data of the photon number received by the CT detector. For example, the target projection data of the intensity domain can be multiplied by the default transform coefficient W (such as, 2) so as to obtain the target projection data of the photon number.

At block B3, the transformed target projection data is used as a Poisson parameter to calculate a Poisson random number, and the Poisson random number is determined as update transformed target projection data.

The target projection data of the photon number is a Poisson distribution with a Poisson parameter $\lambda$, and can be shown in the following formula (2).

$$P(X = i) = \frac{e^{-\lambda}\lambda^i}{i!}; \quad (2)$$

Herein, i is a non-negative integer value 0, 1, 2, . . . , and is a possible value for the transformed photon number; P(X=i) means the probability of the random variable X=i, and is also the probability of the transformed photon number=i; e means a natural base; $\lambda$ means a Poisson parameter of Poisson distribution. The probability distribution of the formula (2) can generate a Poisson random value, and the Poisson random value can be used for replace the target projection data of the photon number, wherein the Poisson random value is equivalent to the target projection data of the photon number containing Poisson noise during acquisition.

At block B4, the update transformed target projection data is transformed to update target projection data of the intensity domain.

The update target projection data of the photon number is then transformed to the data of the intensity domain (such as, divided by the conversion transformed W) so as to obtain update target projection data of the intensity domain.

At block B5, the update target projection data of the intensity domain is converted into update target projection data of the attenuation domain.

The update target projection data I of the intensity domain is converted into update target projection data P of the attenuation domain, and the conversion can be shown in the following formula (3).

$$p = -\log\left(\frac{I}{I_0}\right); \quad (3)$$

Herein, $I_0$ means the original scanning current of X-ray, and I means the update target projection data of the intensity domain.

At block B6, the update target projection data of the attenuation domain is determined as the noise-adjusted target projection data.

The abovementioned blocks B1-B6 is merely an example of adjusting noise level, and there are other possible implementations. In another example, the block of adjusting noise of the corrected target projection data to generate noise-adjusted target projection data to improve noise consistency between target region and the rest of the CT scan image may include the following blocks.

At block C1, a noise value of a Gaussian distribution with zero mean is obtained.

In this example, the Poisson noise of the intensity domain can be replaced with the Gaussian noise of the attenuation domain, and thus the noise level of the corrected target projection data can be directly adjusted. The block of obtaining a noise value of a Gaussian distribution with zero mean can be calculated in the following formula (4).

$$f(x) = \frac{1}{\sqrt{2\pi}\,\sigma}\exp\left(-\frac{(x-\mu)^2}{2\sigma^2}\right); \quad (4)$$

Herein, x is the noise value, f(x) is the probability of occurrence for the noise value x, the mean $\mu=0$, and the variance $\sigma$ can be obtained according to the following formula (5).

$$\sigma_y = \sqrt{\frac{\exp(ul)}{I_0}}; \quad (5)$$

Herein, $\mu l$ means the projection data of the attenuation domain within the metal target region, and $I_0$ means the original scanning current of X-ray.

At block C2, the noise value is summed with the target projection data so as to obtain the noise-adjusted target projection data.

The corrected target projection data is then summed with the noise value obtained at block C1 so as to obtain the noise-adjusted target projection data.

After that, please return to FIG. 1, and enter the block 104, a corrected CT scan image is reconstructed based on the noise-adjusted target projection data.

In an example, the block of reconstructing a corrected CT scan image based on the noise-adjust target projection data may include the following blocks.

At block D1, a first corrected CT scan image is generated based on the noise-adjusted target projection data.

At block D2, the first corrected CT scan image is integrated with the target image so as to generate a second corrected CT scan image.

At the block 102, not only all data for generating metal artefacts is eliminated, but also corresponding data of the metal is eliminated at the same time. Therefore, at this block, the target image containing metal data is integrated with the first corrected CT scan image without the metal image for generating the second corrected CT scan image, such that the data of the metal image itself can be recovered.

Figure 4:
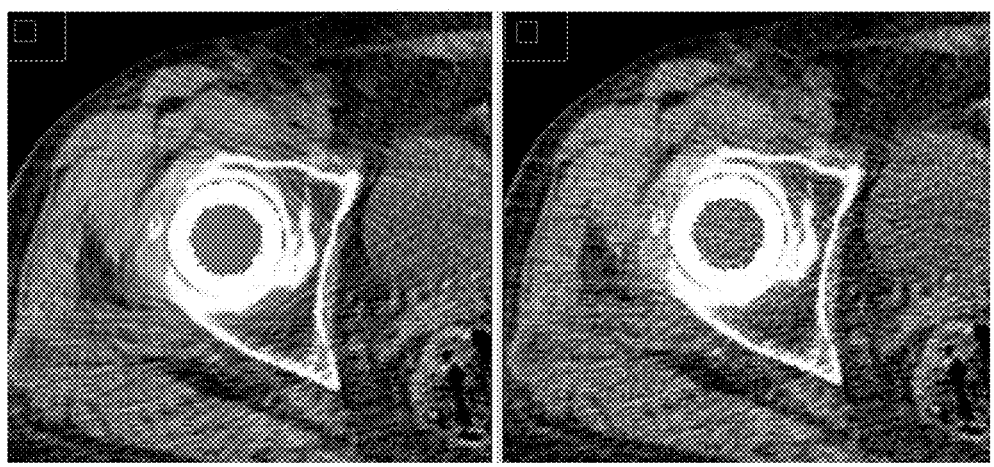
FIG. 4 is an effect drawing for a noise-adjusted CT scan image according to an example of the present disclosure.

FIG. 4 is an effect drawing for a noise-adjusted CT scan image according to an example of the present disclosure. The left figure shown in FIG. 4 is a non-noise-adjusted CT scan image, and the right figure shown in FIG. 4 is a corrected noise-adjusted CT scan image, wherein the image sharpness of the right figure is much better than the image sharpness of the left figure, and the noise consistency and the image quality of the right figure are much better than the noise consistency and the image quality of the left figure.

As can be seen in this example, after correcting the target projection data with greater attenuation (such as, the metal artefact data) to improve noise consistency between target region and the rest of the CT scan image, the noise level of the corrected target projection data is continued to be adjusted in order to ensure that the noise level of the target projection data is consistent with the noise level of other non-target projection data, such that the image quality of the reconstructed CT scan image will be improved due to the whole image noise consistency.

Figure 5:
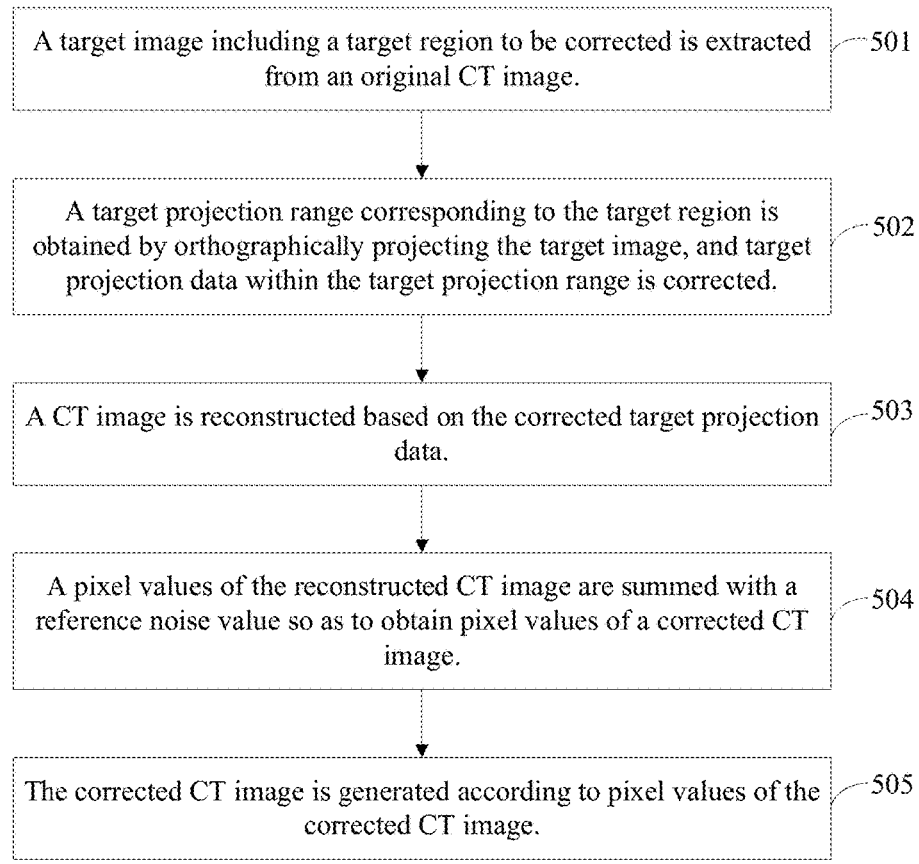
FIG. 5 is a schematic flowchart illustrating the procedures of a method for correcting a CT scan image according to another example of the present disclosure.

Please refer to FIG. 5. FIG. 5 is a flowchart illustrating the procedures of a method for correcting a CT scan image according to another example of the present disclosure. The method may include the following blocks.

At block 501, a target image including a target region to be corrected is extracted from an original CT scan image.

At block 502, a target projection range corresponding to the target region is obtained by orthographically projecting the target image, and target projection data within the target projection range is corrected.

At block 503, a CT scan image is reconstructed based on the corrected target projection data.

At block 504, pixel values of the reconstructed CT scan image are summed with a reference noise value so as to obtain pixel values of a corrected CT scan image.

After the corrected CT scan image is reconstructed, the noise within the image domain can be directly adjusted. In an example, the noise consistency of the target image and the non-target image can be improved to achieve noise consistency in the CT scan image, and pixel values of the reconstructed CT scan image are summed with a reference noise value so as to obtain pixel values of a corrected CT scan image. The reference noise value can be a noise value of a Gaussian distribution with zero mean; and the non-target image can be other parts of the original CT scan image excluding the target image.

For example, if the target image is an image including a metal, the pixel values of the target image can be summed with a noise value of a Gaussian distribution with zero mean, i.e., a noise value of a Gaussian distribution with zero mean may be added into the formula (4).

At block 505, the corrected CT scan image is generated according to pixel values of the corrected CT scan image.

In the present disclosure, after correcting the target projection data with greater attenuation (such as, the metal artefact data) to improve noise consistency between target region and the rest of the CT scan image, the noise level of the corrected target projection data is continued to be adjusted in order to ensure that the noise level of the target projection data is consistent with the noise level of other non-target projection data, such that the image quality of the reconstructed CT scan image will be improved due to the whole image noise consistency. Therefore, a goal of improving the image quality of the reconstructed CT scan image can be achieved.

Figure 6:
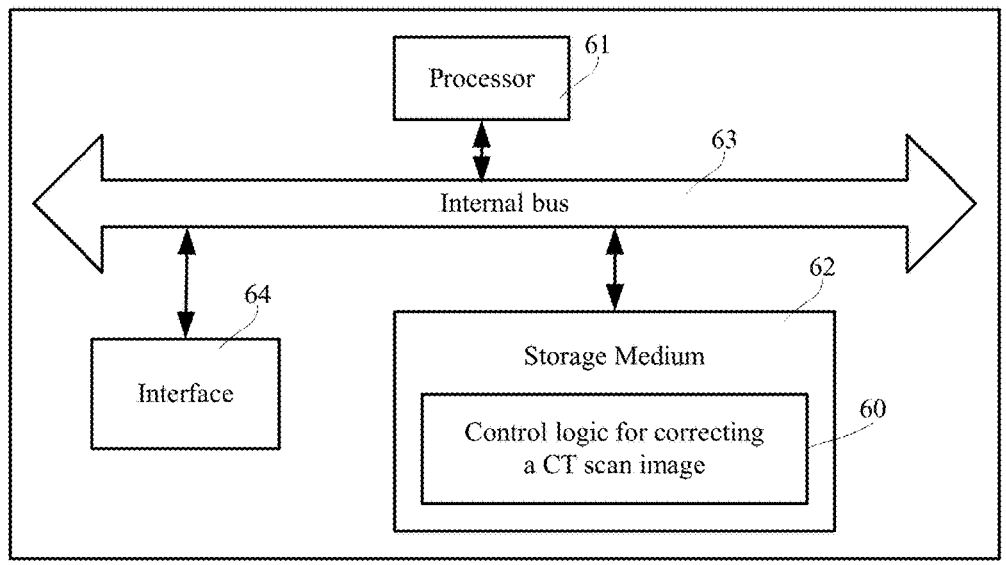
FIG. 6 is a hardware architecture diagram of a device for correcting a CT scan image according to an example of the present disclosure.

In accordance with the abovementioned method, a device for correcting a CT scan image is provided in the present disclosure. Please refer to FIG. 6. In an example, the device may include a processor such as a CPU 61 and a machine readable storage medium 62, wherein the processor 61 is connected to the machine readable storage medium 62 through an internal bus 63. In other possible implementations, the device may further include an interface 64 for communicating with other devices or components.

In different examples, the machine readable storage medium 62 may be Random Access Memory (RAM), volatile memory, non-volatile memory, flash memory, storage drives (such as, hard drive), solid state drive, any type of storage disks (such as, CD-ROM, DVD, etc.), or similar storage medium, or a combination thereof.

Figure 7:
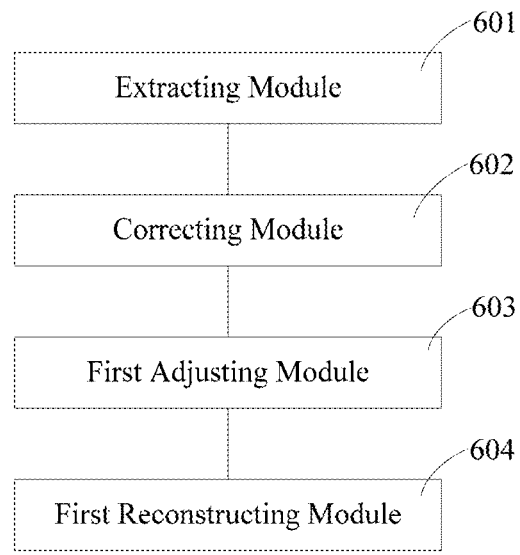
FIG. 7 is a functional block diagram of the control logic for correcting a CT scan image according to an example of the present disclosure.

In an example, the machine readable storage medium 62 is used for storing a control logic 60 for correcting a CT scan image. As shown in FIG. 7, a block diagram of the control logic 60 may further include an extracting module 601, a correcting module 602, a first adjusting module 603, and a first reconstructing module 604.

The extracting module 601 is used for extracting a target image including a target region to be corrected from an original CT scan image.

The correcting module 602 is used for obtaining a target projection range corresponding to the target region by orthographically projecting the target image, and for correcting target projection data within the target projection range.

In a possible implementation, the correcting module 602 may further include: a second obtaining sub-module for obtaining a linear interpolation value of two projection data points located at two adjacent sides of the target projection data; a replacing sub-module for replacing the target projection data with the linear interpolation value so as to obtain corrected data of the target projection data; a reconstructing sub-module for reconstructing a corresponding corrected image according to the corrected data of the target projection data; a third determining sub-module for determining a reference image of the corrected image according to a default segmentation threshold; a projecting sub-module for orthographically projecting the reference image so as to obtain reference projection data of the reference image; and a fourth determining sub-module for determining the reference projection data as the corrected target projection data.

The first adjusting module 603 is used for adjusting noise of the corrected target projection data to generate noise-adjusted target projection data to improve noise consistency between target region and the rest of the CT scan image.

In a possible implementation, the target region to be corrected is a metal region, and the first adjusting module 603 may further include: a first converting sub-module for converting the target projection data of an attenuation domain into target projection data of an intensity domain; a first transforming sub-module for transforming the target projection data of the intensity domain to the target projection data of the photon number; a first determining sub-module for using the target projection data of the photon number as the Poisson parameter to calculate a Poisson random number, and for determining the Poisson random number as the update target projection data of the photon number; a second transforming sub-module for transforming the update projection data of the photon number to update target projection data of the intensity domain; a second converting sub-module for converting the update target projection data of the intensity domain into the update target projection data of the attenuation domain; and a second determining sub-module for determining the update target projection data of the attenuation domain as the noise-adjusted target projection data.

In another example, the target region to be corrected is a metal region, and the first adjusting module 603 may further include: a first obtaining sub-module for obtaining a noise value of a Gaussian distribution with zero mean; and a calculating sub-module for summing the noise value with the target projection data so as to obtain the noise-adjusted target projection data.

The first reconstructing module 604 is used for reconstructing a corrected CT scan image based on the noise-adjusted target projection data.

In an example, the first reconstructing module 604 may further include: a generating sub-module for generating a first corrected CT scan image based on the noise-adjusted target projection data; and an integrating sub-module for integrating the first corrected CT scan image with the target image so as to generate a second corrected CT scan image.

Figure 8:
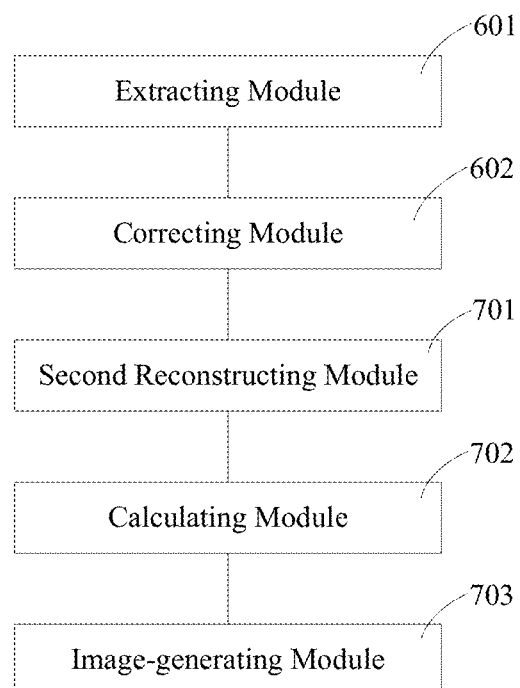
FIG. 8 is a functional block diagram of the control logic for correcting a CT scan image according to another example of the present disclosure.

Please refer to FIG. 8. In another example, the block diagram of the control logic 60 may further include an extracting module 601, a correcting module 602, a second reconstructing module 701, a calculating module 702, and an image-generating module 703.

The extracting module 601 is used for extracting a target image including a target region to be corrected from an original CT scan image.

The correcting module 602 is used for obtaining a target projection range corresponding to the target region by orthographically projecting the target image, and for correcting target projection data within the target projection range.

The second reconstructing module 701 is used for reconstructing a CT scan image based on the corrected target projection data.

The calculating module 702 is used for summing pixel values of the reconstructed CT scan image with a reference noise value so as to obtain pixel values of a corrected CT scan image; wherein the reference noise value is a noise value of a Gaussian distribution with zero mean.

The image-generating module 703 is used for generating the corrected CT scan image according to pixel values of the corrected CT scan image.

The example below is implemented with software, which describes how the device for correcting a CT scan image runs the control logic 60. In this example, the control logic 60 of the present disclosure should be understood as machine readable instructions stored in the machine readable storage medium 62. When the processor 61 of the device for correcting a CT scan image executes the control logic 60, the processor 61 executes machine readable instructions of the control logic 60 stored in the machine readable storage medium 62 to:

extract a target image including a target region to be corrected from an original CT scan image;

obtain a target projection range corresponding to the target region by orthographically projecting the target image, and correct target projection data within the target projection range;

adjust noise of the corrected target projection data to generate noise-adjusted target projection data according to improve noise consistency between target region and the rest of the CT scan image; and reconstruct a corrected CT scan image based on the noise-adjusted target projection data.

In an example, the processor 61 executing machine readable instructions of the control logic 60 for correcting a CT scan image to adjust noise of the corrected target projection data to generate noise-adjusted target projection data causes the processor 61 to:

convert the target projection data of an attenuation domain into target projection data of an intensity domain;

multiplying the target projection data of the intensity domain by the default transform coefficient to obtain a transformed target projection data;

use the transformed target projection data as the Poisson parameter to calculate a Poisson random number, and determine the Poisson random number as the update transformed target projection data;

transform the update transformed projection data to update target projection data of the intensity domain;

convert the update target projection data of the intensity domain into the update target projection data of the attenuation domain; and determine the update target projection data of the attenuation domain as the noise-adjusted target projection data.

In another example, the processor 61 executing machine readable instructions of the control logic 60 for correcting a CT scan image to adjust noise of the corrected target projection data to generate noise-adjusted target projection data to improve noise consistency between target region and the rest of the CT scan image causes the processor 61 to:

obtain a noise value of a Gaussian distribution with zero mean; and sum the noise value with the target projection data so as to obtain the noise-adjusted target projection data.

In an example, the processor 61 executing machine readable instructions of the control logic 60 for correcting a CT scan image to obtain a target projection range corresponding to the target region by orthographically projecting the target image, and to correct target projection data within the target projection range causes the processor 61 to:

obtain a linear interpolation value of two projection data points located at two adjacent sides of the target projection data;

replace the target projection data with the linear interpolation value so as to obtain corrected data of the target projection data;

reconstruct a corresponding corrected image according to the corrected data of the target projection data;

determine a reference image of the corrected image according to a default segmentation threshold;

orthographically project the reference image so as to obtain reference projection data of the reference image; and determine the reference projection data as the corrected target projection data.

In an example, the processor 61 executing machine readable instructions of the control logic 60 for correcting a CT scan image to reconstruct a corrected CT scan image based on the noise-adjusted target projection data causes the processor 61 to:

generate a first corrected CT scan image based on the noise-adjusted target projection data; and integrate the first corrected CT scan image with the target image so as to generate a second corrected CT scan image; wherein the target region to be corrected is the metal region of the subject.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for correcting a CT scan image, the method comprising:
    extracting a target image including a target region to be corrected from an original CT scan image;
    obtaining a target projection range corresponding to the target region by orthographically projecting the target image, and correcting target projection data within the target projection range to obtain corrected target projection data;
    generating noise-adjusted target projection data by adjusting noise of the corrected target projection data according to target projection data of an intensity domain which is obtained from target projection data of an attenuation domain, so as to improve noise consistency between the target region and rest of the CT original scan image; and
    reconstructing a corrected CT scan image based on the noise-adjusted target projection data;
    wherein adjusting noise of the corrected target projection data to generate the noise-adjusted target projection data comprises:
        converting the target projection data of the attenuation domain into the target projection data of the intensity domain;
        multiplying the target projection data of the intensity domain by a default transform coefficient so as to obtain a transformed target projection data;
        using the transformed target projection data as a Poisson parameter to calculate a Poisson random number, and determining update transformed target projection data based on the Poisson random number;
        transforming the update transformed target projection data to update target projection data of the intensity domain;
        converting the update target projection data of the intensity domain into update target projection data of the attenuation domain; and
        determining the update target projection data of the attenuation domain as the noise-adjusted target projection data.

2. The method of claim 1, wherein obtaining a target projection range corresponding to the target region by orthographically projecting the target image, and correcting target projection data within the target projection range comprises:
    obtaining a linear interpolation value of two projection data points located at two adjacent sides of the target projection data;
    replacing the target projection data with the linear interpolation value so as to obtain corrected data of the target projection data;
    reconstructing a corresponding corrected image according to the corrected data of the target projection data;
    determining a reference image of the corrected image according to a default segmentation threshold;
    orthographically projecting the reference image so as to obtain reference projection data of the reference image; and
    determining the reference projection data as the corrected target projection data.

3. The method of claim 1, wherein reconstructing a corrected CT scan image based on the noise-adjusted target projection data comprises:
    generating a first corrected CT scan image based on the noise-adjusted target projection data; and
    integrating the first corrected CT scan image with the target image so as to generate a second corrected CT scan image.

4. The method of claim 1, wherein the target region to be corrected is a metal region.

5. The method of claim 1, wherein determining update transformed target projection data based on the Poisson random number includes using the Poisson random number as the update transformed target projection data.

6. A device for correcting a CT scan image, the device comprising:
    a processor configured to execute machine readable instructions corresponding to a control logic for correcting a CT scan image stored on a storage medium, wherein the machine readable instructions, when executed by the processor, cause the processor to:
    extract a target image including a target region to be corrected from an original CT scan image;
    obtain a target projection range corresponding to the target region by orthographically projecting the target image, and correct target projection data within the target projection range to obtain corrected target projection data;
    generate noise-adjusted target projection data by adjusting noise of the corrected target projection data according to target projection data of an intensity domain which is obtained from target projection data of an attenuation domain, so as to generate noise-adjusted target projection data to improve noise consistency between the target region and rest of the CT original scan image; and
    reconstruct a corrected CT scan image based on the noise-adjusted target projection data
    wherein when adjusting noise of the corrected target projection data to generate the noise-adjusted target projection data, said machine readable instructions further cause the processor to:
        convert the target projection data of the attenuation domain into the target projection data of the intensity domain;
        multiply the target projection data of the intensity domain by a default transform coefficient so as to obtain transformed target projection data;
        use the transformed target projection data as a Poisson parameter to calculate a Poisson random number, and determine update transformed target projection data based on the Poisson random number;
        transform the update converted target projection data to update target projection data of the intensity domain;
        convert the update target projection data of the intensity domain into update target projection data of the attenuation domain; and
        determine the update target projection data of the attenuation domain as the noise-adjusted target projection data.

7. The device according to claim 6, wherein said machine readable instructions further cause the processor to:

obtain a linear interpolation value of two projection data points located at two adjacent sides of the target projection data;

replace the target projection data with the linear interpolation value so as to obtain corrected data of the target projection data;

reconstruct a corresponding corrected image according to the corrected data of the target projection data;

determine a reference image of the corrected image according to a default segmentation threshold;

orthographically project the reference image so as to obtain reference projection data of the reference image; and determine the reference projection data as the corrected target projection data.

8. The device according to claim 6, wherein said machine readable instructions further cause the processor to:

generate a first corrected CT scan image based on the noise-adjusted target projection data; and integrate the first corrected CT scan image with the target image so as to generate a second corrected CT scan image.

9. The device according to claim 6, wherein the target region to be corrected is a metal region.

10. The device of claim 6, wherein determining update transformed target projection data based on the Poisson random number includes using the Poisson random number as the update transformed target projection data.

* * * * *